United States Patent
Walters

(10) Patent No.: US 10,857,320 B2
(45) Date of Patent: Dec. 8, 2020

(54) PRE-CUT ADHESIVE STRIPS FOR SECURING AIRWAY TUBES

(71) Applicant: Christopher Walters, Duxbury, MA (US)

(72) Inventor: Christopher Walters, Duxbury, MA (US)

( * ) Notice: Subject to any disclaimer, the term of this patent is extended or adjusted under 35 U.S.C. 154(b) by 188 days.

(21) Appl. No.: 15/955,746

(22) Filed: Apr. 18, 2018

(65) Prior Publication Data

US 2019/0076616 A1    Mar. 14, 2019

Related U.S. Application Data

(60) Provisional application No. 62/606,109, filed on Sep. 11, 2017.

(51) Int. Cl.
*A61M 16/06*    (2006.01)
*A61M 16/04*    (2006.01)

(52) U.S. Cl.
CPC .... *A61M 16/0688* (2014.02); *A61M 16/0497* (2013.01); *A61M 2205/0216* (2013.01); *A61M 2210/0618* (2013.01); *A61M 2210/0625* (2013.01)

(58) Field of Classification Search
CPC .......... A61M 16/0488; A61M 16/0497; A61M 16/0688; A61M 25/02; A61M 2025/022; A61M 2025/0226; A61M 2025/0253; A61M 2025/026; A61M 2025/0266; A61M 16/0461
See application file for complete search history.

(56) References Cited

U.S. PATENT DOCUMENTS

| 3,677,250 | A | * | 7/1972 | Thomas | A61M 25/02 604/180 |
| 3,927,676 | A | * | 12/1975 | Schultz | A61M 25/02 128/207.17 |
| 5,038,778 | A | | 8/1991 | Lott | |
| 5,221,265 | A | * | 6/1993 | List | A61M 25/02 128/DIG. 26 |
| 5,448,985 | A | * | 9/1995 | Byrd | A61M 16/0488 128/207.17 |
| 5,468,231 | A | * | 11/1995 | Newman | A61M 25/02 604/180 |
| 5,671,732 | A | * | 9/1997 | Bowen | A61M 16/0465 128/207.17 |

(Continued)

OTHER PUBLICATIONS

Sharn Anesthesia, Inc., *Product Catalog*, edition 22, vol. 1 (no date given).

*Primary Examiner* — Valerie L Woodward
(74) *Attorney, Agent, or Firm* — Ryuh Patent Law; Steven Yu

(57) ABSTRACT

An adhesive strip that could be used for securing oral or nasal airway tubes, such as endotracheal tubes or laryngeal mask airways. The adhesive strip has an elongated shape and is coated on one side with an adhesive material. At each terminal end of the adhesive strip, there is a non-adhesive tab that is free of the adhesive material. The non-adhesive tabs facilitate removal of the adhesive strip off the release liner and/or off the patient's skin. The adhesive strip can be used by adhering onto the patient's face and wrapping it around the airway tube to secure the airway tube.

8 Claims, 3 Drawing Sheets

(56) References Cited

U.S. PATENT DOCUMENTS

| | | | | |
|---|---|---|---|---|
| 5,797,884 | A * | 8/1998 | Byrd | A61M 25/02 604/174 |
| 7,544,186 | B2 * | 6/2009 | Davis | A61M 25/02 128/DIG. 26 |
| 8,230,862 | B2 * | 7/2012 | McInnes | A61M 25/02 128/207.11 |
| 8,794,240 | B1 * | 8/2014 | Marcoe | A61M 16/0447 128/207.14 |
| 9,968,760 | B2 * | 5/2018 | Chawki | A61M 25/02 |
| 2017/0112676 | A1 | 4/2017 | Williams et al. | |
| 2017/0173287 | A1 * | 6/2017 | Kotzian | A61B 50/30 |

* cited by examiner

PRE-CUT ADHESIVE STRIPS FOR SECURING AIRWAY TUBES

RELATED APPLICATIONS

This application claims the benefit of U.S. Provisional Patent Application No. 62/606,109 filed on Sep. 11, 2017, the contents of which are incorporated herein by reference.

TECHNICAL FIELD

This invention relates to adhesive tapes, and more particularly to adhesive tapes used in securing endotracheal tubes.

BACKGROUND

Although accidental extubation is an uncommon event, loss of the airway from an inadequately secured endotracheal tube can occur, leading to potentially serious complications. The most frequently used method of securing endotracheal tubes is by taping the tube to the patient's face. In many operating rooms, the endotracheal tube is secured with conventional medical tape.

However, rolls of tape used in operating rooms are often dirty and contaminated from repeated use on multiple patients. Unfortunately, anesthesia clinicians who handle the tape rolls are often non-compliant with hand hygiene. Moreover, the rolls of tape are often dropped on the floor, where they pick up dirt and pathogens. Thus, the use of conventional roll tape increases the patient's exposure to pathogens and the risk of infection.

SUMMARY

This invention provides an adhesive strip that could be used for securing oral or nasal airway tubes, such as endotracheal tubes or laryngeal mask airways. The adhesive strip has an elongated shape. In some embodiments, the length of the adhesive strip is in the range of 15-60 cm, and in some cases, in the range of 20-45 cm long. In some embodiments, the width of the tape strip is in the range of 1.0-4.0 cm. In some embodiments, the length/width ratio of the adhesive strip is in the range of 7-30, and in some cases, 11-30.

Backing Layer:

The adhesive strip comprises a flexible, thin, elongated backing layer in the shape of a long strip. Any suitable type of backing layer could be used, including those that are commercially available. Examples of backing layers (also sometimes referred to as backing laminates, backing films, etc.) that could be used include polymeric films of polyester, polypropylene, polyethylene, ethylene/vinyl acetate copolymers, polyvinyl chloride, polyvinyl acetate, polyurethane, paper, foams, non-woven fabric, or woven cloth.

In some embodiments, the backing layer is optically transparent. The backing layer may be designated as being optically transparent for the product as marketed (such as the 3M SCOTCHPAK 1022 transparent fluoropolymer-coated polyester film). In some embodiments, the total transmittance of broadband visible light (390-700 nm wavelength) orthogonally incident upon the backing layer or release liner is at least 70%. The term "optically transparent" includes translucency. There may or may not be distortion in the transmitted light.

Adhesive Material:

One side of the backing layer (i.e. the bottom side) is coated with an adhesive material. The adhesive material may comprise a single adhesive compound or a mixture of different adhesives compounds. Any suitable type of skin-adhering adhesive may be used. Examples of adhesive materials that could be used include acrylic adhesives, silicone adhesives, elastomeric (rubber-based) adhesives, block copolymer adhesives, polyisobutene adhesives, urethane adhesives, polybutadiene adhesives, poly(ethylene-vinyl acetate) (PEVA) adhesives, polyvinyl ether adhesives, and hydrocolloids and gelatins such as karaya gum, guara gum, collagen, polysaccharide gum, locust bean gum, powdered pectin, gelatin, carboxymethyl cellulose, etc. Preferably, the adhesive material provides a fluid-resistant seal for the adhesive strip.

Non-Adhesive Tabs:

The adhesive strip further comprises two non-adhesive tabs, one at each terminal end of the adhesive strip. The non-adhesive tabs do not have a coating of adhesive material. This facilitates removal of the adhesive strip off the release liner and/or off the patient's skin. In some embodiments, the non-adhesive tabs have a visible indicia that visibly differentiates it from the main body of the adhesive strip. As used herein, "main body" means the portion of the adhesive strip that is between the non-adhesives tabs. Any suitable type of indicia may be used. For example, the indicia may be a different color, different shade, markings (e.g. cross-hatching), printed pattern, words, etc. In some embodiments, the length of the non-adhesive tab is in the range of 0.5-3.0 cm.

Adhesive Strip Assembly:

In another aspect, the invention provides an adhesive strip assembly that comprises one or more adhesive strips that are mounted on a release liner. The adhesive strip is intended to be easily separable from the release liner so that the adhesive strip can be applied onto the patient's skin. In some embodiments, there are multiple (two or more) adhesive strips on a single release liner (e.g. adhesive strips provided as a set). In some cases, the multiple adhesive strips are arranged side-by-side on the release liner with the longitudinal axes of the adhesive strips substantially parallel to each other.

Materials suitable for use as release liners are well-known and include paper fabric, polyethylene, polyvinylchloride, polyethylene terephthalate, polyester, metalized laminate, polypropylene, and polystyrene. The material for the release liner may be coated with silicone or fluoropolymer to facilitate detachment. The release liner may be provided as a single unitary sheet or as multiple sheets (e.g. as two abutting sheets).

Method of Use:

In another aspect, the invention provides a method of using an adhesive strip to secure an airway tube. In one embodiment, an adhesive strip assembly is provided and the user lifts a non-adhesive tab to peel the adhesive strip off the release liner. A first portion of adhesive strip is adhered onto the patient's face. A middle portion of the adhesive strip is wrapped around the airway tube. As used herein, "middle portion" means the middle one-third portion of the adhesive strip if the adhesive strip were to be divided into three equal parts. The other (second) portion of the adhesive strip is adhered onto the patient's face.

In some embodiments, both the first and second portions of the adhesive strip are placed on the same lateral side. For example, both the first and second portions may be adhered to the left side of the face, or both adhered to the right side of the face.

In some embodiments, a second adhesive strip is used to further secure the airway tube. The user lifts a non-adhesive tab to peel the second adhesive strip off its release liner. A first portion of the second adhesive strip is adhered onto the patient's face. A middle portion of the second adhesive strip is wrapped around the airway tube. The other (second) portion of second adhesive strip is adhered onto the patient's face.

In some embodiments, both the first and second portions of the second adhesive strip are placed on the same lateral side of the patient's face. In some embodiments, the second adhesive strip is placed on the other lateral side of the patient's face as the first adhesive strip. For example, if the first adhesive strip is placed onto the left side of the patient's face, then the second adhesive strip is placed onto the right side of the patient's face.

The non-adhesive tabs on the adhesive strip may allow for easy removal off the patient's face. As such, in some embodiments, the method further comprises removing the adhesive strip off the patient. This is performed by lifting up on a non-adhesive tab and peeling the adhesive strip off the patient's skin.

BRIEF DESCRIPTION OF THE DRAWINGS

FIG. 1A shows a top view of the adhesive strip. FIG. 1B shows an adhesive strip assembly in which the adhesive strip is mounted on a release liner. FIG. 1C shows a side view of the adhesive strip assembly.

DETAILED DESCRIPTION

Figure 1A:
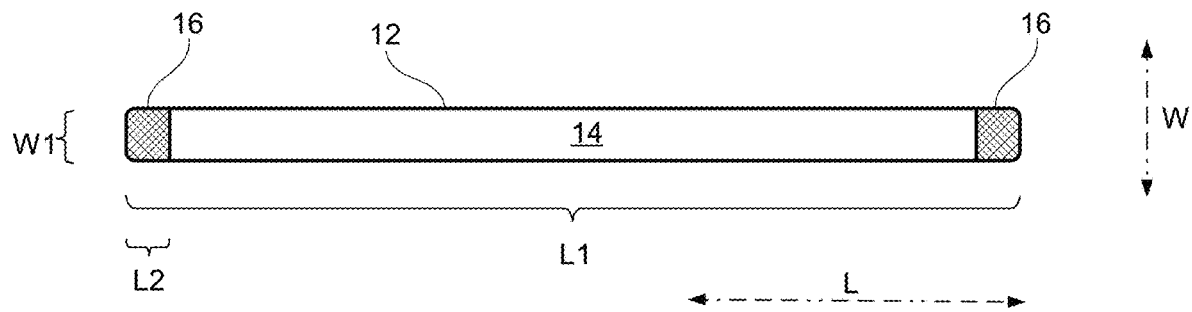
FIGS. 1A-C show an example adhesive strip of the invention.
Figure 1B:
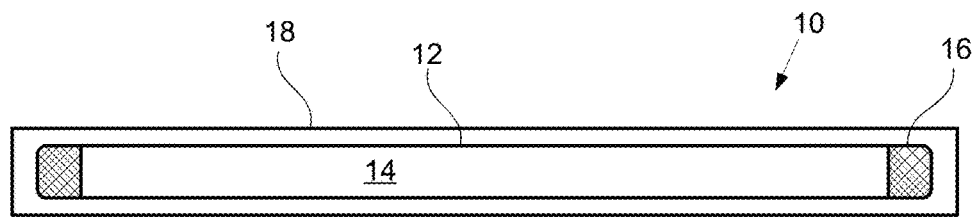
Figure 1C:
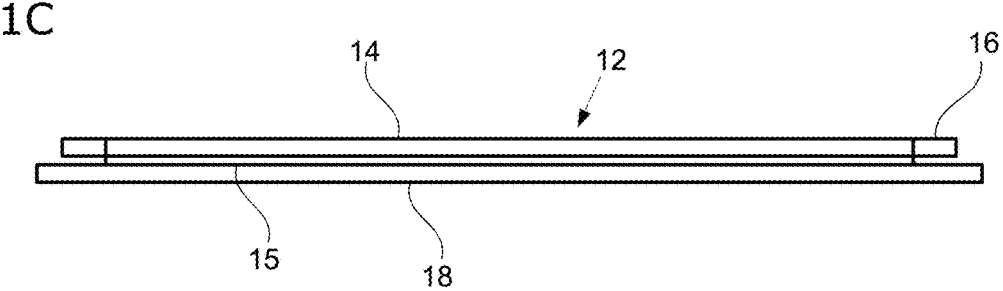

To assist in understanding the invention, reference is made to the accompanying drawings to shown by way of illustration specific embodiments in which the invention may be practiced. FIGS. 1A-C show an example embodiment of the invention. FIG. 1A (top view) shows an adhesive strip 12 alone. The adhesive strip 12 comprises a backing layer 14. On the bottom side of the backing layer 14, there is an adhesive material 15 (see FIG. 1C below). At each terminal end of the adhesive strip 12, there is a non-adhesive tab 16 in which the backing layer 14 is free of the adhesive material 15. The non-adhesive tabs 16 are marked with blue cross-hatching to differentiate it from the main body of the adhesive strip 12.

FIG. 1A also shows the dimensions of the adhesive strip 12. For definition herein, the length of an adhesive strip of the invention or parts thereof is measured along the longitudinal axis as indicated by the line "L"; and the width of an adhesive strip of the invention or parts thereof is measured along the transverse axis as indicated by the line "W." Here, the width W1 is about 2 cm. The length L1 of the adhesive strip is about 30 cm. The length/width ratio is about 15. The length L2 of the non-adhesive tab is about 1.8 cm long.

FIG. 1B shows an adhesive strip assembly 10 in which the adhesive strip 12 is mounted on a release liner 18. The user peels the adhesive strip 12 off of release liner 18 by lifting up the non-adhesive tab 16 and pulling the adhesive strip 12 away from the release liner 18. FIG. 1C shows a side view of the adhesive strip assembly 10. As seen in this view, the adhesive material 15 is applied onto the bottom surface of the backing layer 14. By this adhesive material 15, the adhesive strip 12 is mounted onto the release liner 18.

Figure 2A:
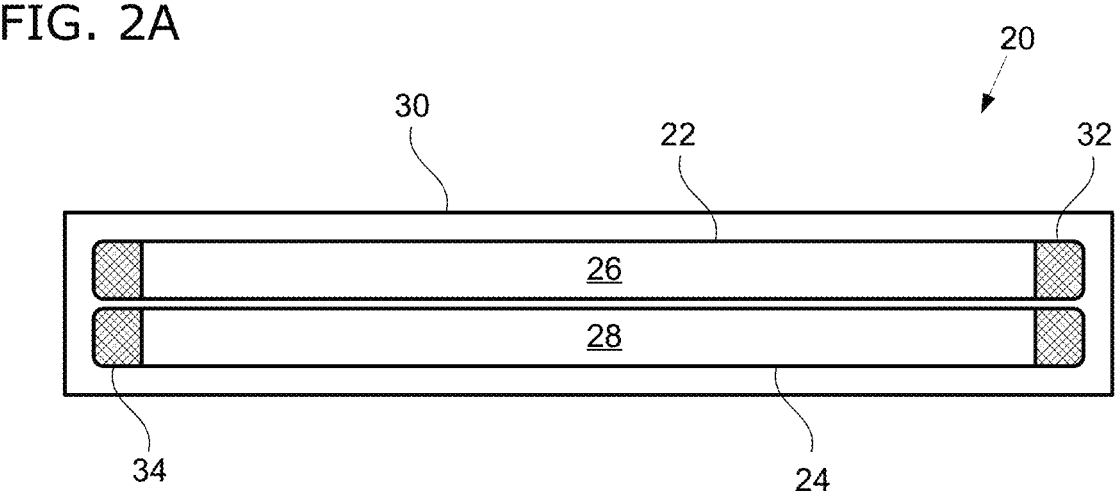
FIGS. 2A and 2B show an example adhesive strip assembly comprising a pair of adhesive strips.
Figure 2B:
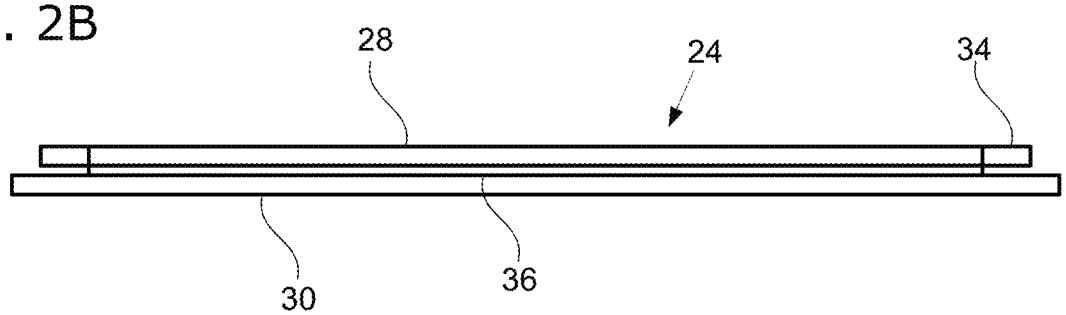

FIGS. 2A and 2B show another example embodiment of the invention. FIG. 2A (top view) shows an adhesive strip assembly 20 in which a pair of adhesive strips 22 and 24 are mounted onto a release liner 30. Each adhesive strip 22 and 24 is made using a backing layer 26 and 28. On the bottom side of each backing layer 26 and 28, there is adhesive material 36 (see FIG. 2B below). At the terminal ends of adhesive strips 22 and 24, there are non-adhesive tabs 32 and 34 in which the backing layer 26 and 28 are free of the adhesive material 36. The non-adhesive tabs 32 and 34 are marked with blue cross-hatching to differentiate it from the main body of the adhesive strips 22 and 24.

FIG. 2B shows a side view of the adhesive strip assembly 20 (only adhesive strip 24 is visible in this view). As seen in this view, the adhesive material 36 is applied onto the bottom surface of the backing layer 28. By this adhesive material 36, the adhesive strip 24 is mounted onto the release liner 30.

Figure 3:
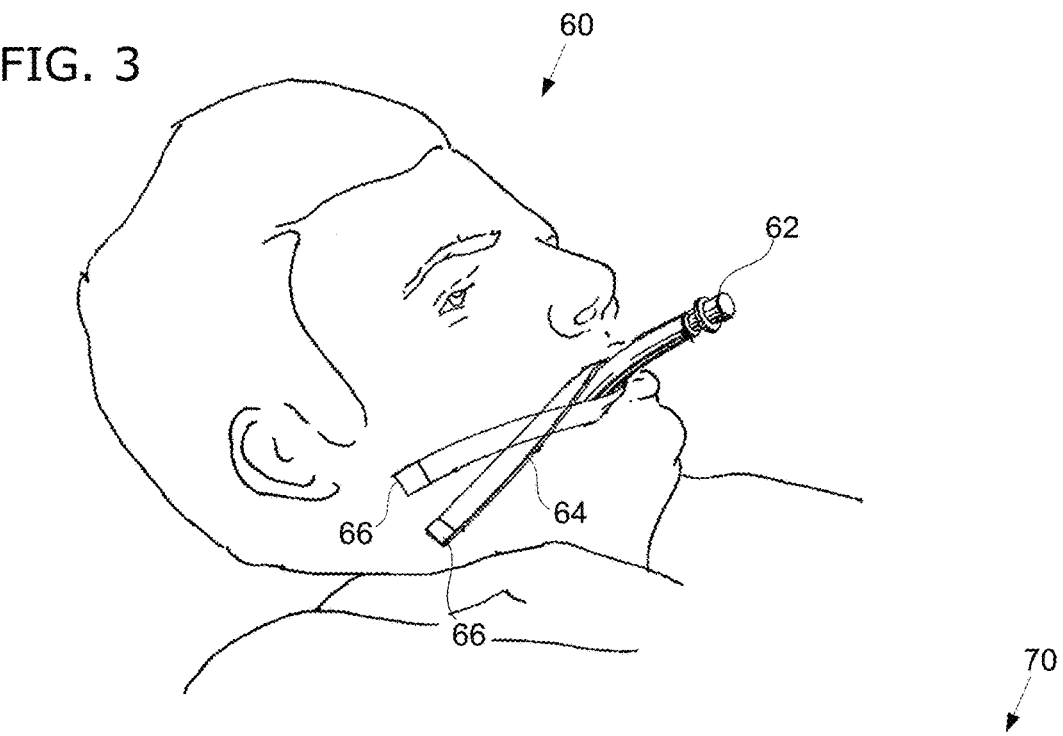
FIG. 3 shows an example of how an adhesive strip could be used to secure an endotracheal tube.

FIG. 3 shows another example embodiment of the invention in which the user (e.g. an anesthesiologist) uses a transparent adhesive strip 64 to secure an endotracheal tube 62. Here, the patient 60 has an orally-inserted endotracheal tube 62. The user peels the adhesive strip 64 off of its release liner by lifting up a non-adhesive tab 66 and pulling the adhesive strip 64 away from the release liner. One portion of the adhesive strip 64 is adhered onto the patient's face (with the adhesive side facing the skin). The adhesive strip 64 is then wrapped around the endotracheal tube 62 and adhered thereto. The other (second) portion of adhesive strip 64 is then adhered onto the patient's face on the same lateral side as the first portion.

The non-adhesive tabs 66 also allow easy removal of the adhesive strip 64 off the patient's face. When the endotracheal tube 62 is ready to be removed, the adhesive strip 64 is peeled off the patient's skin by lifting up a non-adhesive tab 66 and peeling the adhesive strip 64 off the patient's skin.

Figure 4:
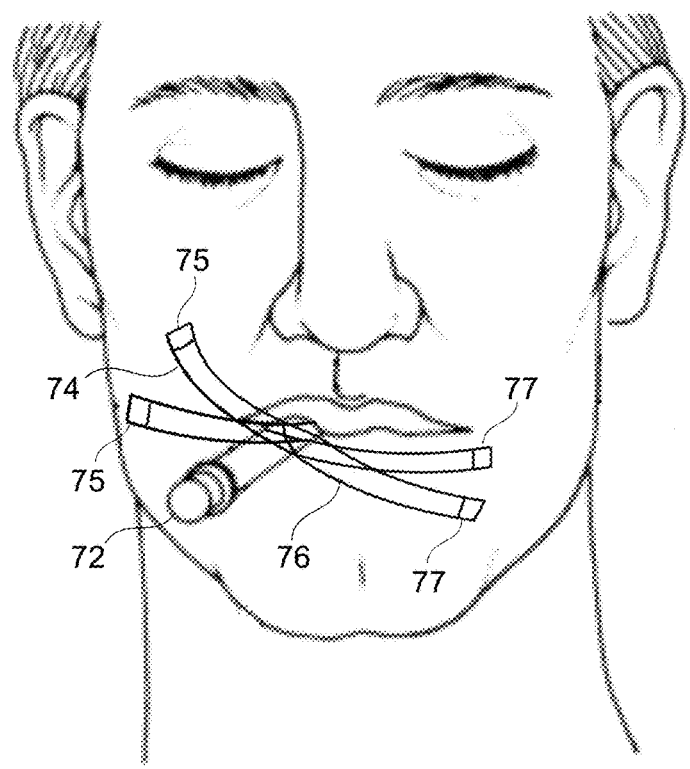
FIG. 4 shows an example of how a pair of adhesive strips could be used to secure an endotracheal tube.

FIG. 4 shows another example embodiment of the invention in which a pair of transparent adhesive strips 74 and 76 are used to secure the endotracheal tube 72. Here, the patient 70 has an orally-inserted endotracheal tube 72. The user peels the adhesive strip 74 off its release liner by lifting up a non-adhesive tab 75 and pulling the adhesive strip 74 away from the release liner. One portion of the adhesive strip 74 is adhered onto the patient's face (with the adhesive side facing the skin). The adhesive strip 74 is then wrapped around the endotracheal tube 72 and adhered thereto. The other (second) portion of adhesive strip 74 is then adhered onto the patient's face on the same lateral side of the face as the first portion.

The second adhesive strip 76 is applied in the same manner as the first adhesive strip 74, except that it is applied on the other lateral side of the face. The user lifts up on non-adhesive tab 77 to peel adhesive strip 76 off its release liner, adheres one portion onto the patient's face, wraps it around the endotracheal tube 72, and then adheres the other (second) portion onto the patient's face on the same lateral side of the face as the first portion.

The foregoing description and examples have been set forth merely to illustrate the invention and are not intended to be limiting. Each of the disclosed aspects and embodiments of the invention may be considered individually or in combination with other aspects, embodiments, and variations of the invention. In addition, unless otherwise specified, the steps of the methods of the invention are not confined to any particular order of performance. Modifications of the disclosed embodiments incorporating the spirit and substance of the invention may occur to persons skilled in the art, and such modifications are within the scope of the invention.

Any use of the word "or" herein is intended to be inclusive and is equivalent to the expression "and/or," unless the context clearly dictates otherwise. As such, for example, the expression "A or B" means A, or B, or both A and B. Similarly, for example, the expression "A, B, or C" means A, or B, or C, or any combination thereof.

The invention claimed is:

1. In a patient having an airway tube, a method of securing the airway tube, comprising steps (i)-(ix) in the following order of performance:
   (i) having an adhesive strip assembly comprising:
      a first elongated adhesive strip and a second elongated adhesive strip, wherein each adhesive strip comprises:
         a flexible backing layer;
         an adhesive material on one side of the backing layer;
         a first non-adhesive tab at one end of the adhesive strip that is free of the adhesive material; and
         a second non-adhesive tab at the other end of the adhesive strip that is free of the adhesive material; and
      a single, continuous release liner onto which the first and second adhesive strips are mounted;
   (ii) pulling one of the first or second non-adhesive tabs of the first adhesive strip to peel the first adhesive strip off the release liner;
   (iii) adhering a first portion of the first adhesive strip onto a first lateral side of the patient's face;
   (iv) wrapping a middle portion of the first adhesive strip around the airway tube;
   (v) adhering a second portion of the first adhesive strip onto the first lateral side of the patient's face;
   (vi) pulling one of the first or second non-adhesive tabs of the second adhesive strip to peel the second adhesive strip off the release liner;
   (vii) adhering a first portion of the second adhesive strip onto a second lateral side of the patient's face;
   (viii) wrapping a middle portion of the second adhesive strip around the airway tube; and
   (ix) adhering a second portion of the second adhesive strip onto the second lateral side of the patient's face.

2. The method of claim 1, wherein each of the adhesive strips has: a length in the range of 15-60 cm; a width in the range of 1.0-4.0 cm; a length/width ratio in the range of 7-30.

3. The method of claim 1, further comprising peeling each of the adhesive strips off the patient's face by pulling on one of the first or second non-adhesive tabs of each adhesive strip.

4. The method of claim 1, wherein the airway tube is an endotracheal tube or a laryngeal mask airway.

5. The method of claim 1, wherein each of the adhesive strips has: a length in the range of 20-45 cm; a length/width ratio in the range of 11-30.

6. The method of claim 1, wherein each backing layer is transparent.

7. The method of claim 1, wherein the first tabs and the second tabs have indicia that distinguish them from the middle portion of the adhesive strips.

8. The method of claim 1, wherein the first tabs and the second tabs each have a length in the range of 0.5-3.0 cm.

* * * * *